United States Patent [19]

Crassous et al.

[11] Patent Number: 4,781,838

[45] Date of Patent: Nov. 1, 1988

[54] SOLID POLYVINYL ALCOHOL-BASED SUPPORT ABLE TO ADSORB LIPOPROTEINS AND ITS USE FOR THE SEPARATION OF LOW DENSITY LIPOPROTEINS PRESENT IN A LIQUID, SUCH AS BLOOD PLASMA

[75] Inventors: Geneviève Crassous, Paris; Gilbert Gaussens, Meudon; Dominique Duval, Courbevoie; Maryvonne Nicaise, Saint Remy Les Chevreuse; Gérard Vergne, Antony; Sylvaine Hours, Paris, all of France

[73] Assignee: Commissariat A L'Energie Atomique, Paris, France

[21] Appl. No.: 897,751

[22] Filed: Aug. 18, 1986

[30] Foreign Application Priority Data

Aug. 23, 1985 [FR] France .................. 85 12666

[51] Int. Cl.⁴ ............. B01D 15/00; C08G 18/10
[52] U.S. Cl. .................... 210/692; 210/502.1;
210/905; 210/908; 502/5; 502/402; 521/53;
521/140; 521/149; 521/150
[58] Field of Search .............. 210/679, 692, 905, 908,
210/927, 502.1; 502/401, 402, 5; 525/56–62;
536/59, 118; 521/53, 140, 149, 150; 530/359

[56] References Cited

U.S. PATENT DOCUMENTS

| | | | |
|---|---|---|---|
| 4,314,032 | 2/1982 | Murayama et al. | 525/60 X |
| 4,423,184 | 12/1983 | Kopolow et al. | 525/61 X |
| 4,430,229 | 2/1984 | Yamawaki et al. | 210/692 |
| 4,432,871 | 2/1984 | Yamawaki et al. | 210/927 X |
| 4,576,927 | 3/1986 | Kuroda et al. | 502/402 |
| 4,576,928 | 3/1986 | Tani et al. | 502/401 X |
| 4,654,420 | 3/1987 | Furuyoshi et al. | 536/118 |
| 4,721,572 | 1/1988 | Jordan | 502/401 |

FOREIGN PATENT DOCUMENTS

| | | |
|---|---|---|
| 0110409 | 6/1984 | European Pat. Off. . |
| 0143369 | 6/1985 | European Pat. Off. . |
| 0180168 | 5/1986 | European Pat. Off. . |
| 2343251 | 9/1977 | France . |
| 936039 | 6/1960 | United Kingdom . |

OTHER PUBLICATIONS

Journal of Polymer Science: Part A vol. 3, pp. 3405-3512 (1965) Bruce A. Bernstein et al., Radiation Crosslinking of Nylon 66 and Poly (vinyl Alcohol).

Primary Examiner—Richard V. Fisher
Assistant Examiner—W. Gary Jones
Attorney, Agent, or Firm—Pearne, Gordon, McCoy & Granger

[57] ABSTRACT

This support is constituted by a crosslinked polyvinyl alcohol hydrogel, whereof at least part of the —OH groups have been replaced by —OSO₃H groups. The crosslinked polyvinyl alcohol hydrogel comprises 70 to 95% by weight of chains derived from polyvinyl alcohol and 5 to 30% by weight of chains derived from crosslinking monomers, such as triethylene glycol diacrylate and tetraethylene glycol triacrylate.

These supports can be used for the ex-vivo purification of the blood plasma in pocket 31 or 33.

14 Claims, 2 Drawing Sheets

SOLID POLYVINYL ALCOHOL-BASED SUPPORT ABLE TO ADSORB LIPOPROTEINS AND ITS USE FOR THE SEPARATION OF LOW DENSITY LIPOPROTEINS PRESENT IN A LIQUID, SUCH AS BLOOD PLASMA

BACKGROUND OF THE INVENTION

The present invention relates to a solid support able to adsorb lipoproteins, particularly low density lipoproteins present in a liquid, such as blood plasma. More specifically the invention relates to polyvinyl alcohol-based insoluble supports usable for the selective purification of low density lipoproteins in the blood plasma by selective adsorption.

The amount of low density lipoproteins is abnormally high in the blood of patients suffering from hypercholesterolemia, which can lead to risks of early cardiac accidents through serious vascular lesions due to the accumulation of these lipoproteins. Moreover, processes making it possible to purify the blood plasma of such patients by adsorption of low density lipoproteins on solid supports are of great interest, because at present there is no process of this type for carrying out this purification operation. Thus, hitherto plasmapheresis processes have been used and consist of partly substituting the plasma of the patient by a foreign plasma or by a replacement solution. In addition, the development of direct purification processes of the patient's plasma has formed the subject matter of a large amount of research justified by the interest in avoiding foreign plasma injections and the need of maintaining the indispensable constituent plasma elements at the desired levels.

SUMMARY OF THE INVENTION

The present invention relates to a polyvinyl alcohol-based solid support able to selectively separate low density lipoproteins present in a liquid and which can be used for carrying out the ex-vivo lipoprotein purification of the blood plasma of a patient suffering from hypercholesterolemia.

The present invention therefore specifically relates to a solid support able to adsorb lipoproteins, wherein it is constituted by a polyvinyl alcohol hydrogel crosslinked by irradiation with at least one crosslinking monomer having at least two reactive ethylene functions under ionizing radiation, said crosslinked polyvinyl alcohol hydrogel having 70 to 95% by weight of chains derived from polyvinyl alcohol and 5 to 30% by weight of chains derived from crosslinking monomers and at least part of the —OH groups of the polyvinyl alcohol hydrogel are replaced by —OSO$_3$H groups directly fixed onto carbon atoms of the hydrogel.

The use of a crosslinked polyvinyl alcohol hydrogel makes the support insoluble in most solvents, particularly in water and aqueous solutions, which is indispensable when it is wished to use such a support in separation processes by adsorption in aqueous solution. Crosslinking also makes it possible to obtain an insoluble product able to mechanically resist the action of solutions with which it could be contacted, e.g. it does not decompose in a solution, such as blood plasma. Moreover, through carrying out said crosslinking by irradiation using crosslinking monomers makes it possible to better control the degree of crosslinking and to ensure that the —OSO$_3$H groups fixed to the crosslinked polyvinyl alcohol remain accessible. Thus, the presence of crosslinking monomers and irradiation makes it possible to obtain an insoluble support having a swelling in aqueous solutions greater than that of polyvinyl alcohol supports crosslinked without the addition of crosslinking monomers. This is an important advantage because it gives a better accessibility to the —OSO$_3$H groups and consequently there is a better adsorption of the low density lipoproteins.

Thus, the presence of —OSO$_3$H groups gives the support a specific affinity for lipoproteins which generally have the special feature of forming stable complexes with polyanions via ionic bonds between the negatively charged groups of the polyanions such as SO$_3^-$COO$^-$ and NHSO$_3^-$ and the positive groups of the protein part of lipoproteins such as NH$_2^+$.

Preferably, the degree of crosslinking of the polyvinyl alcohol is not too high so that the hydrogel retains the property of swelling in water, e.g. in liquids such as the physiological serum. However, it is necessary for the degree of crosslinking to be adequate to obtain the desired insolubility properties in water.

These two results are obtained when the support comprises 70 to 95% by weight of chains derived from polyvinyl alcohol and 5 to 30% by weight of chains derived from crosslinking monomers having at least two reactive ethylene functions under ionizing radiation. Generally, the crosslinking monomers are polyacrylic or polymethacrylic monomers.

Examples of such monomers are polyol polyacrylates and polymethacrylates, such as ethylene glycol diacrylate, triethylene glycol diacrylate or triacrylate, tetraethylene glycol diacrylate, trimethylol propane triacrylate, ethylene glycol dimethacrylate, triethylene glycol dimethacrylate, tetraethylene glycol dimethacrylate, trimethylol propane trimethacrylate, pentaerythritol tetraacrylate, pentaerythritol tetramethacrylate and mixtures thereof.

According to a preferred embodiment of the invention the crosslinking monomers are tetraethylene glycol diacrylate and triethylene glycol diacrylate.

Generally, the supports accord to the invention are used in the form of powders having a grain size distribution of 50 to 100 μm and preferably 63 to 100 μm.

In the supports according to the invention, the quantity of —OSO$_3$H groups fixed to the support in particular determines the affinity of the support with respect to lipoproteins. This affinity increases with the number of —OSO$_3$H groups and to obtain an adequate affinity, it is necessary for the support to have at least 15% by weight —OSO$_3$H groups. In general, goods results are obtained when the support comprises 33 to 45% by weight of —OSO$_3$H groups.

The invention also relates to a process for the preparation of a solid support having the aforementioned characteristics. This process comprises the following stages:

(a) crosslinking the polyvinyl alcohol by subjecting irradiation by means of ionizing rays a mixture comprising 70 to 95% by weight of polyvinyl alcohol and 5 to 30% by weight of at least one crosslinking monomer in an oxygen-free atmosphere and (b) subjecting the thus obtained crosslinked polyvinyl alcohol to a chlorosulphonation treatment for replacing at least part of the —OH groups of the polyvinyl alcohol by —OSO$_3$H groups.

According to the invention, the crosslinking of the polyvinyl alcohol is on the one hand performed by means of ionizing rays and on the other by reacting with a crosslinking monomer having at least two reactive ethylene functions under ionizing rays. In this case, a mixture of polyvinyl alcohol and crosslinking monomers is subject to irradiation by ionizing rays in an oxygen-free atmosphere. Generally, the polyvinyl alcohol is in aqueous solution and to the latter is added the crosslinking monomers, which can in particular be constituted by the aforementioned monomers.

In the process according to the invention, the choice of the polyvinyl alcohol used as the starting product is also important, because the molecular weight thereof has an affect on the results obtained, particularly on the degree of swelling in the water of the support and on the degree of adsorption of the lipoproteins.

Preference is given to the use of a polyvinyl alcohol having in a 4% solution in water a viscosity of 3.5 to 5 mPa.s.

For crosslinking purposes, the ionizing rays which can be used are e.g. ultraviolet rays, X-rays, $\alpha$, $\beta$ or $\gamma$ rays and accelerated electron beams.

Advantageously use is made of the rays from a cobalt 60 source or electron beams. It is also possible to obtain crosslinking chemically, e.g. by using $Ce^{4+}$ ions.

In the process of the invention, the parameters making it possible to act on the degree of crosslinking are:
the polyvinyl alcohol concentration of the aqueous solution,
the irradiation dose,
the irradiation dose rate,
the quantity of crosslinking monomers used.

When the polyvinyl alcohol is irradiated in aqueous solution, the polyvinyl alcohol concentration of the solution is preferably 25 to 30% by weight.

As has been shown hereinbefore, the quantity of crosslinking monomers used represents at the most 30% by weight of the mixture of polyvinyl alcohol and crosslinking monomers, in order to then obtain an adequate affinity of the support for the lipoproteins.

The irradiation doses and the irradiation dose rates used are chosen as a function of the desired degree of crosslinking. When the crosslinking monomers are added to the polyvinyl alcohol, account is also taken of the quantity of crosslinking monomers used for choosing the irradiation doses and dose rates, so as to obtain the desired degree of crosslinking.

In general, when using gamma rays, the total irradiation doses are 8 to 16 Mrad and the radiation dose rates 0.2 to 0.5 $Mrad.h^{-1}$.

The second stage of the process according to the invention consisting of the chlorosulphonation of the crosslinked polyvinyl alcohol is generally performed in a pyridine medium by reacting the polymer with the pyridinium sulphate complex. This complex is prepared in situ by the slow addition of chlorosulphonic acid to the pyridine kept at 0° C. This is followed by the addition of the crosslinked polyvinyl alcohol and the reaction is continued hot, e.g. at 70° C., accompanied by stirring.

The duration of the reaction is chosen as a function of the quantity of —$OSO_3H$ groups which it is wished to fix to the crosslinked polyvinyl alcohol.

Following this reaction, the hydrogel is separated from the solution and it is subjected to a number of washing operations, e.g. using methanol-soda mixtures. The hydrogel obtained is then dried in an oven, ground and screened to the desired grain size, it being kept in the dry state. Prior to being used as a lipoprotein adsorbing support, the polymer powder is swollen beforehand in the physiological serum.

The present invention also relates to a process for the separation of low density lipoproteins present in a liquid. This process consists of contacting the liquid with the solid support according to the invention and then separating the liquid from the support on which have been adsorbed the low density lipoproteins. The liquid can be blood or blood plasma.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
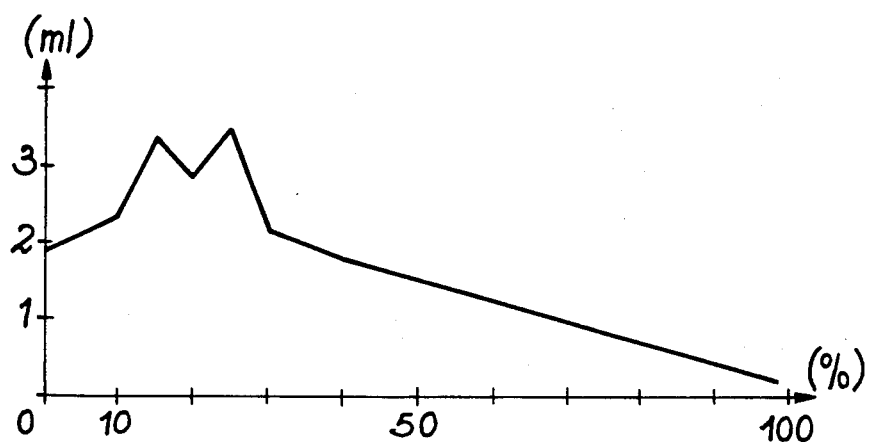
FIG. 1, a graph showing the influence of the quantity of crosslinking monomers on the degree of swelling of the supports in the physiological serum.

The following exemplified embodiments are given for the purpose of illustrating the invention. In all these examples, the supports are constituted by polyvinyl alcohol hydrogels crosslinked under irradiation with a mixture of tetraethylene glycol diacrylate and triethylene glycol diacrylate (DIATEG).

EXAMPLES TO 5

In these examples, the starting product is polyvinyl alcohol having in a 4% aqueous solution a viscosity of 3.5 to 5 mPa.s. and said polyvinyl alcohol is crosslinked by subjecting an aqueous solution containing 30% by weight of polyvinyl alcohol to which is added DIATEG (mixture of triethylene glycol diacrylate and tetraethylene glycol diacrylate), so that the DIATEG/polyvinyl alcohol mixture contains 10 to 40% by weight of DIATEG and 60 to 90% by weight of PVA. Irradiation by electron beams takes place in such a way that the total radiation dose is 12 Mrad with a mean dose rate of 134 $Mrad.h^{-1}$. Following this stage, the crosslinked polyvinyl alcohol undergoes chlorosulphonation by contacting the crosslinked polyvinyl alcohol with a solution of chlorosulphonic acid and pyridine with 12% chlorosulphonic acid, for three hours, at 70° C. and accompanied by stirring. This is followed by washing the hydrogel with mixtures of methanol and soda, drying in an oven, grinding and screening in order to collect a powder with a grain size of 63 to 80 μm, which is then kept in the dry state. The number of —$OSO_3H$ groups fixed to the support is then determined on the basis of the amount of sulphur determined by elementary analysis (EA).

The properties of the thus obtained support are then checked for the separation of lipoproteins from the blood plasma. For this purpose, the powder is firstly immersed in physiological serum to swell it and then the lipoprotein adsorption tests are performed. For the purpose of these tests, use is made of a closed dish, into which is introduced one ml of the powder support and 3 ml of the plasma to be purified containing the lipoproteins. Permanent rotary stirring thereof is maintained and incubation takes place for 30 minutes at ambient temperature.

At the end of the reaction, the plasma is separated from the support by decanting or centrifuging and determination takes place of the levels of the lipoproteins: total cholesterol $C_T$ and high density lipoproteins ($C_{HDL}$) in the plasma. The lipoprotein level is also determined before carrying out the purification treatment.

In this way the purification level obtained is deduced. The following procedure is adopted for determining the different levels. The total cholesterol level $C_T$ is determined by colorimetric dosing after enzymatic hydrolysis using the SIGMA kit and the method described in Allain. CA, Poon. LS, Cran C.S.G, Richmond W, Fu PC., Clin. Chem, 20, p. 470 (74) Enzymatic determination of total serum cholesterol. The high density lipoprotein level $C_{HDL}$) is determined by colorimetric dosing in the supernatant following selective precipitation of the low density lipoproteins and very low density lipoproteins by sodium phosphotungstate in the presence of $MgCl_2$. The triglyceride level $T_G$ of the plasma is determined by ultraviolet dosing following enzymatic hydrolysis using the SIGMA kit. After carrying out those dosing operations, it is possible to deduce therefrom the level of low density lipoproteins $C_{LDL}$ by using the formula:

$$C_{LDL} = C_T - C_{HDL} - (T_G/5)$$

After carrying out these measurements, the purification capacity of the support is determined, this corresponding to the total cholesterol quantity $C_T$ (in mg) fixed per ml of swollen support in the physiological serum. The purification level is given by the percentage of fixed $C_T$ determined from $C_T$ plasma concentrates before and after purification. The adsorption level of the adsorbed high density lipoproteins $C_{HDL}$ is checked. A check is also made on the amount of low density lipoproteins $C_{LDL}$ adsorbed and the amount of triglycerides $T_G$. The results obtained are given in table 1, which also gives the support production conditions. The table shows that the purification capacity decreases when the crosslinking agent proportion increases. Moreover, it has been found that the adsorption of high density lipoproteins never exceeds 20% of the initial value thereof in the plasma. Thus, the supports have a good selectivity for low density lipoproteins.

EXAMPLES 6 TO 8

In these examples, use is made of the same operating procedure as in example 1 for producing and testing supports prepared from the same polyvinyl alcohol and DIATEG, but in this case the total radiation dose is varied by using a 20% DIATEG content in the PVA—DIATEG mixture. Following the chlorosulphonation treatment, the powder with a grain size of 63 to 100 μm is collected, its content of —OSO₃H groups determined and the lipoproteins undergo adsorption tests under the same conditions as in examples 1 to 5. The results obtained are given in table 1.

On the basis of these results, it can be seen that the purification capacity decreases when the radiation dose increases, i.e. when the degree of crosslinking increases.

EXAMPLES 9 TO 15

In these examples use is made of the same polyvinyl alcohol and the same operating procedure as in example 1 for preparing the crosslinked polyvinyl alcohol and for carrying out the chlorosulphonation treatment, but the DIATEG content of the PVA—DIATEG mixture is varied from 0 to 40% and a radiation dose of 10 Mrad is applied in the case where there is no DIATEG and 14 Mrad in the case where crosslinking takes place with DIATEG. The content of —OSO₃H groups is then measured, as is the purification capacity of the support for lipoproteins, as defined in example 1. The degree of swelling of the supports in the physiological serum (S$\phi$) is also determined. The results obtained are given in table 2 and FIG. 1 representing the variations of the degree of swelling (in ml) of 100 mg of support as a function of the DIATEG content (percent by weight).

FIG. 1 shows that the swelling of the support is greater when the DIATEG content is 5 to 30%. This improvement of the swelling is a very interesting property of the supports according to the invention, because it makes it possible to obtain a better accessibility of the —OSO₃H groups used for the purification of the low density lipoproteins. This improvement is obtained as a result of the addition of crosslinking monomers.

The results of table 2 also show that the crosslinking level is better when the proportion of DIATEG does not exceed 25% and this also applies with respect to the degree of swelling.

EXAMPLE 16 TO 25

These examples study the influence of the grain size distribution of the support particles on the purification capacity. As in example 1, the supports are prepared starting with the same PVA, but using 15, 20 or 25% by weight DIATEG and carrying out irradiation by means of gamma rays from a cobalt 60 source with a total dose of 14 Mrad and a dose rate of 0.23 Mrad.h$^{-1}$. Following the chlorosulphonation treatment, which is carried under the same conditions as in example 1, the thus obtained polyvinyl alcohol hydrogel is washed, dried, ground and screened. Separation takes of the fractions having grain sizes from 50 to 63, 63 to 80, 80 to 100 and 100 to 200 μm, use then being made of each of these grain size fractions for carrying out lipoprotein adsorption tests using the same test conditions as in example 1. The results obtained are given in table 3.

On the basis of these results, it can be seen that the purification capacity is significantly better when the grain size of the support is 50 to 80 μm.

EXAMPLES 26 TO 29

Figure 2:
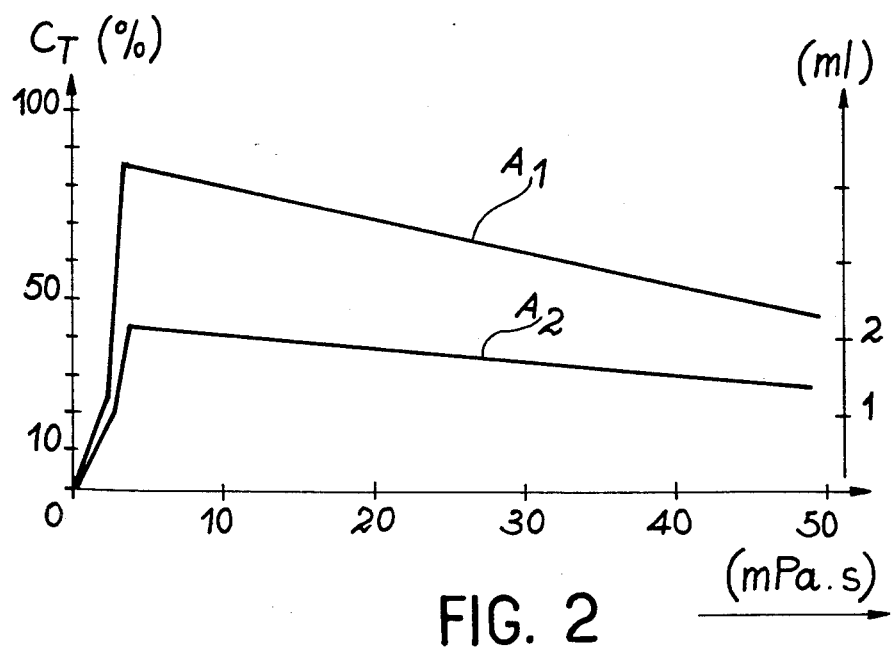
FIG. 2, a graph showing the influence of the viscosity of the polyvinyl alcohol on the total cholesterol purification percentage (curve 1) and on the degree of swelling in the physiological serum (curve 2).

These examples study the influence of the molecular weight of the starting polyvinyl alcohol on the result obtained. The starting polyvinyl alcohols are commercial products, whose viscosity in a 4% aqueous solution can vary from 2.6 to 48 mPa.s. These supports are crosslinked by irradiation using gamma rays from a cobalt 60 source with 25% DIATEG, a total radiation dose of 14 Mrad and a dose rate of 0.23 Mrad.h$^{-1}$. The crosslinked hydrogels obtained in this way then undergo a chlorosulphonation treatment performed under the same conditions as in example 1. The fraction having a grain size distribution of 60 to 100 μm is separated and the degree of swelling (in ml) of 100 mg of support in the physiological serum and the purification capacity of the lipoproteins are determined. The results obtained are given in table 4 and in curves $A_1$ and $A_2$ of FIG. 2, which respectively represent the variations of the purification capacity $C_T$ (in percent) and the swelling (in ml) of 100 mg of support in the physiological serum, as a function of the viscosity (in mPa.s) of the initial polyvinyl alcohol.

These results show that the degree of swelling and the purification capacity are better when the viscosity of the starting polyvinyl alcohol varies from 3.5 to 5 mPa.s.

EXAMPLE 30

Figure 3:
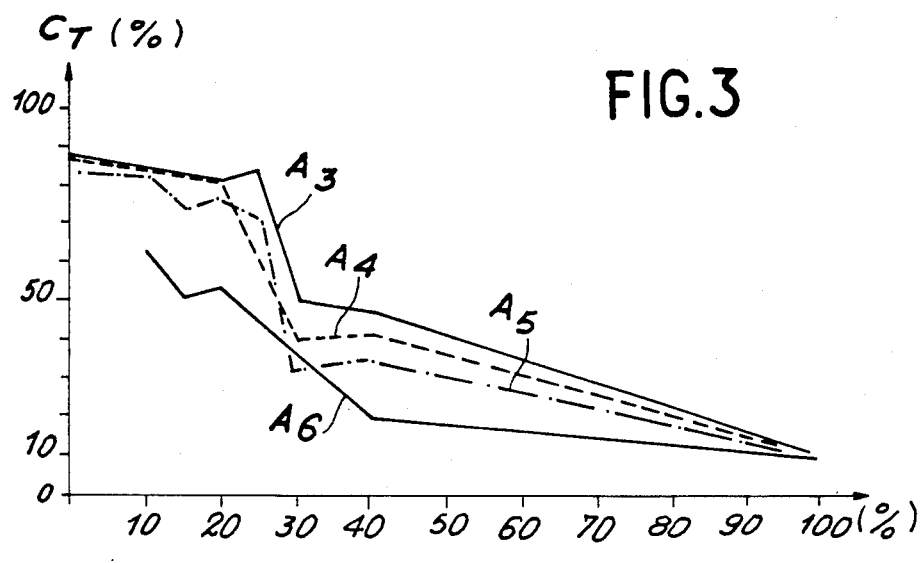
FIG. 3, a graph showing the influence of the amount of crosslinking monomers on the total cholesterol purification percentage for different radiation doses.

This example uses the operating procedure of example 1 and a study is made of the influence of the DIATEG content (in percent) and the irradiation conditions on the purification capacity $C_T$ (in percent) of the solid supports obtained. The results are given in FIG. 3, where curves $A_3$ to $A_5$ respectively refer to tests performed on powder supports with a grain size of 50 to 63 μm for curve $A_3$, 63 to 80 μm for curve $A_4$ and 100 to 800 μm for curve $A_5$, irradiation taking place with a total dose of 14 Mrad using gamma rays.

Curve $A_6$ refers to tests performed on a powder support with a grain size of 63 to 800 μm irradiated by means of an electron beam with a total dose of 12 Mrad.

This figure shows that the best results are obtained when the DIATEG quantity is below 25%. Moreover, irradiation by means of gamma rays makes it possible to obtain better results than irradiation by means of an electron beam.

EXAMPLE 31

This example again uses the operating procedure of example 1 for producing a support from the same polyvinyl alcohol, but using as the crosslinking monomer pentaerythritol tetramethacrylate (TMPTA), the content of the latter in the PVA—TMPTA mixture being 8.5% by weight. Irradiation takes place by means of gamma rays from a cobalt 60 source with a total irradiation of 14 Mrad.

Following the chlorosulphonation treatment carried out under the same conditions as those of example 1, the fraction with a grain size of 63 to 100 μm is collected and in the manner described hereinbefore the degree of swelling of 100 mg of support in the physiological serum and the purification capacity of the support for lipoproteins are determined. The results obtained are given in table 5.

EXAMPLE 32

The operating procedure of example 1 is again used for producing a support from the same polyvinyl alcohol, but using as the crosslinking monomer pentaerythritol tetraacrylate (TTPE), the TTPE content of the PVA—TTPE mixture being 8.5% by weight. Irradiation take place by means of gamma rays from a cobalt 60 source with a total radiation dose of 14 Mrad.

Following the chlorosulphonation treatment carried out under the same conditions as in example 1, the fraction with a grain size of 63 to 100 μm is collected and, as hereinbefore, determination takes place of the degree of swelling in the physiological serum of 100 g of support and the purification capacity of the support for lipoproteins. The results obtained are given in table 6.

Figure 4:
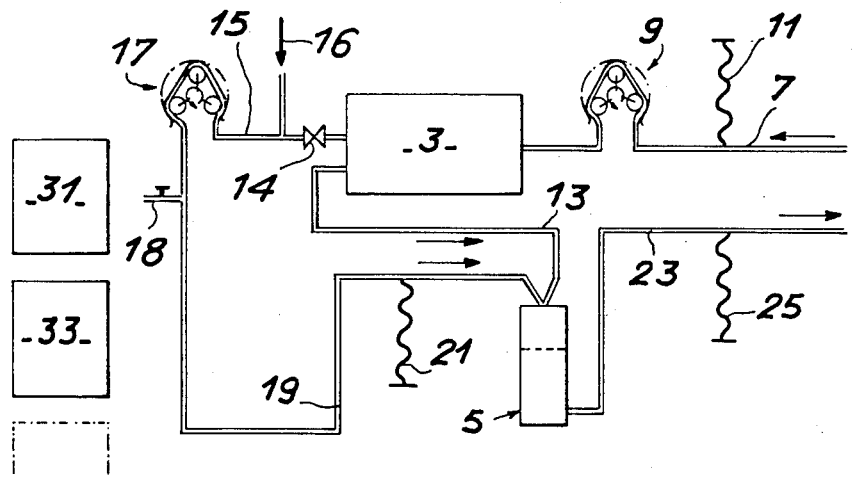
FIG. 4, diagrammatically a plasma purifier for performing the process according to the invention.

The supports according to the invention can be used for the purification of the whole blood or the blood plasma in the purifier shown in FIG. 4. FIG. 4 shows that the purifier comprises a cell separator 3 for separating the blood plasma from the blood to be purified and a collector 5, into which are introduced the cells separated (in 3) from the blood to be treated and also the purified plasma.

In this installation, a first pipe 7 equipped with a pump 9 and a pressure measuring means 11 are used for introducing the blood from the patient into the cell separator 3. In said separator, the cells are discharged by pipe 13 to collector 5, whilst the plasma is directed into pipe 15 equipped with a pump 17. The latter is then extracted from the circuit by the removal valve 18 and then introduced into one of the pockets 31 or 33 containing the adsorbing support according to the invention in order to be purified therein. Following purification, the purified plasma is introduced again upstream of pump 17 by pipe 16 and then valve 14 is closed. The latter is then discharged by pipe 19 provided with a pressure measuring means 21 into collector 5, which also constitutes a safety system for preventing the presence of bubbles in the thus reconstituted blood. The latter is then discharged by pipe 23 equipped with a pressure measuring means 25 into the patient's circulation system.

TABLE 1

| EXAMPLES | % BY WEIGHT OF DIATEG IN THE PVA - DIATEG MIXTURE | RADIATION DOSE (Mrad) | GRAIN SIZE (μm) | % BY WEIGHT OF SULPHUR (EA) | PURIFICATION CAPACITY | | | | | | | |
|---|---|---|---|---|---|---|---|---|---|---|---|---|
| | | | | | $C_T$ (mg/ml) of support | $C_T$ (%) | $C_{HDL}$ (mg/ml) of support | $C_{HDL}$ (%) | $T_G$ (mg/ml) of support | $T_G$ (%) | $C_{LDL}$ (mg/ml of support) | $C_{LDL}$ (%) |
| 1 | 10 | 12 | 63–80 | 13.8 | 5.5 | 64 | 0.093 | 20 | 0.36 | 25.5 | 5.33 | 68 |
| 2 | 15 | 12 | 63–80 | 13 | 4.4 | 50 | 0.126 | 27 | 0.27 | 19 | 4.22 | 52 |
| 3 | 20 | 12 | 63–80 | 15 | 4 | 54 | 0.093 | 20 | 0.18 | 13 | 3.87 | 58 |
| 4 | 25 | 12 | 63–80 | 15 | 5 | 58 | 0.135 | 29 | 0.60 | 42.5 | 4.75 | 60 |
| 5 | 40 | 12 | 63–80 | 11.5 | 1.9 | 21 | 0.135 | 29 | 0.21 | 15 | 1.72 | 21 |
| 6 | 20 | 8.8 | 63–100 | 14.5 | 5 | 70 | 0.069 | 15 | 0.55 | 39 | 4.82 | 75 |
| 7 | 20 | 12 | 63–100 | 15 | 4 | 54 | 0.093 | 20 | 0.18 | 13 | 3.87 | 58 |
| 8 | 20 | 16 | 63–100 | 15 | 1 | 18 | 0.075 | 16 | 0.20 | 14 | 0.90 | 18 |

TABLE 2

| EXAMPLES | % by weight of DIATEG IN PVA - DIATEG MIXTURE | RADIATION DOSE (Mrad) | SWELLING IN PHYSIOLOGICAL SERUM (in ml) | % by weight Sulphur (EA) | PURIFICATION CAPACITY | | | | | | | |
|---|---|---|---|---|---|---|---|---|---|---|---|---|
| | | | | | $C_T$ mg/ml of support | (%) | $C_{HDL}$ mg/ml of support | (%) | $T_G$ mg/ml of support | (%) | $C_{LDL}$ mg/ml of support | (%) |
| 9 | 0 | 10 | 1.9 | 12 | 7.5 | 85 | 0.105 | 22 | 0.108 | 8 | 7.4 | 91 |

TABLE 2-continued

| EXAMPLES | % by weight of DIATEG IN PVA - DIATEG MIXTURE | RADIATION DOSE (Mrad) | SWELLING IN PHYSIOLOGICAL SERUM (in ml) | % by weight Sulphur (EA) | PURIFICATION CAPACITY | | | | | | | |
|---|---|---|---|---|---|---|---|---|---|---|---|---|
| | | | | | $C_T$ mg/ml of support | (%) | $C_{HDL}$ mg/ml of support | (%) | $T_G$ mg/ml of support | (%) | $C_{LDL}$ mg/ml of support | (%) |
| 10 | 10 | 14 | 2.3 | 11.5 | 7.2 | 83 | 0.135 | 29 | 0.48 | 34 | 7 | 88 |
| 11 | 15 | 14 | 3.3 | 13.5 | 7 | 80 | 0.120 | 26 | 0.63 | 45 | 6.8 | 84 |
| 12 | 20 | 14 | 2.9 | 13.7 | 7 | 80 | 0.105 | 22 | 0.55 | 39 | 6.8 | 84 |
| 13 | 25 | 14 | 3.4 | 13 | 7 | 80. | 0.174 | 37 | 0.75 | 53 | 6.7 | 83 |
| 14 | 30 | 14 | 2.2 | 13 | 3.5 | 39 | 0.186 | 40 | 0.48 | 34 | 3.22 | 39 |
| 15 | 40 | 14 | 1.8 | 12 | 4.5 | 12 | 0.195 | 42 | 0.51 | 36 | 4.20 | 11 |

TABLE 3

| EXAMPLES | % by weight of DIATEG in the PVA - DIATEG mixture | Radiation dose (Mrad) | Grain size (μm) |
|---|---|---|---|
| 16 | 15 | 14 | 80–100 |
| 17 | | | 63–80 |
| 18 | | | 50–63 |
| 19 | 20 | 14 | 100–200 |
| 20 | | | 80–100 |
| 21 | | | 63–80 |
| 22 | | | 50–63 |
| 23 | 25 | 14 | 80–100 |
| 24 | | | 63–80 |
| 25 | | | 50–63 |

| EXAMPLES | PURIFICATION CAPACITY | | | |
|---|---|---|---|---|
| | $C_T$ (mg/ml of support) | $C_T$ (%) | $C_{HDL}$ (mg/ml of support) | $C_{HDL}$ (%) |
| 16 | 6.5 | 75 | 0.135 | 24 |
| 17 | 6.9 | 80 | 0.09 | 16 |
| 18 | 7 | 82 | 0.10 | 19 |
| 19 | 5 | 48 | 0.06 | 11 |
| 20 | 6.6 | 77 | 0.09 | 16 |
| 21 | 7 | 80 | 0.075 | 13.5 |
| 22 | 7 | 80 | 0.10 | 19 |
| 23 | 6 | 71 | 0.09 | 16 |
| 24 | 7 | 80 | 0.075 | 13.5 |
| 25 | 7.4 | 84 | 0.075 | 13.5 |

TABLE 4

| EXAMPLES | PVA | Viscosity in 4% solution (mPa.s) | Degree of swelling (ml) | Purification capacity $C_T$ (%) |
|---|---|---|---|---|
| 26 | Mowiol 3-83 | 2.6 | 1.1 | 25 |
| 27 | Rhodoviol 4-125 | 3.5–5 | 2.2 | 86 |
| 28 | Polyviol* G04-20 | 4 | 2.1 | 87 |
| 29 | Polyviol* G48-20 | 48 | 1.4 | 47 |

*Polyviol G04-20: degree of polymerization in number = 400
*Polyviol G48-20: degree of polymerization in number = 2000

TABLE 5

| EXAMPLE | % by weight of TMPTA in PVA - TMPTA mixture | Radiation dose (Mrad) | Grain size (μm) | Swelling in physiological serum (in ml) | PURIFICATION CAPACITY | | | | | | | |
|---|---|---|---|---|---|---|---|---|---|---|---|---|
| | | | | | $C_T$ (mg/ml) of support | $C_T$ (%) | $C_{HDL}$ (mg/ml) of support | $C_{HDL}$ (%) | $T_G$ (mg/ml) of support | $T_G$ (%) | $C_{LDL}$ mg/ml of support | $C_{LDL}$ (%) |
| 31 | 8.5 | 14 | 63–100 | 3.1 | 2 | 20 | 0.18 | 33 | 1.44 | 35 | 2 | 19 |

TABLE 6

| EXAMPLE | % by weight of TTPE in PVA - TTPE mixture | Radiation dose (Mrad) | Grain size (μm) | Swelling in physiological serum (in ml) | Purification capacity | |
|---|---|---|---|---|---|---|
| | | | | | $C_T$ mg/ml of support | $C_T$ (%) |
| 32 | 8.5 | 14 | 63–100 | 3.7 | 2.5 | 25 |

What is claimed is:

1. A process for the separation of lipoproteins present in a liquid comprising contacting said liquid with a solid support comprising a polyvinyl alcohol hydrogel crosslinked by irradiation with at least one crosslinking monomer having at least two reactive ethylene functions under ionizing radiation, said crosslinked polyvinyl alcohol hydrogel having 70 to 95% by weight of chains derived from polyvinyl alcohol and 5 to 30% by weight of chains derived from crosslinking monomers and at least part of the —OH groups of the polyvinyl alcohol hydrogel are replaced by —OSO$_3$H groups directly fixed onto carbon atoms of the hydrogel and then separating the liquid from the support on which the lipoproteins have been adsorbed.

2. A process according to claim 1, wherein the liquid is blood.

3. A process according to claim 1 wherein the liquid is blood plasma.

4. A solid support able to adsorb lipoproteins, comprising a polyvinyl alcohol hydrogel crosslinked by irradiation with at least one crosslinking monomer having at least two reactive ethylene functions under ionizing radiation, said crosslinked polyvinyl alcohol hydrogel having 70 to 95% by weight of chains derived from polyvinyl alcohol and 5 to 30% by weight of chains derived from crosslinking monomers and at least part of the —OH groups of the polyvinyl alcohol hydrogel are replaced by —OSO$_3$H groups directly fixed onto carbon atoms of the hydrogel.

5. A support according to claim 4, wherein the crosslinking monomers are chosen from among ethylene glycol diacrylate, triethylene glycol diacrylate, tetraethylene glycol diacrylate or triacrylate, trimethylol propane triacrylate, ethylene glycol dimethacrylate, triethylene glycol dimethacrylate, tetraethylene glycol dimethacrylate, trimethylol propane trimethacrylate, pentaethrythritol tetraacrylate, pentaerythritol tetramethacrylate and mixtures thereof.

6. A solid support according to claim 4, wherein the crosslinking monomers are triethylene glycol diacrylate and tetraethylene glycol diacrylate.

7. A solid support according to claim 4, wherein it comprises at least 15% by weight of $-OSO_3H$ groups.

8. A solid support according to claim 4, wherein it is in the form of a powder having a grain size distribution of 50 to 100 μm.

9. A process for the preparation of a solid support for adsorbing lipoproteins, comprising a polyvinyl alcohol hydrogel crosslinked by irradiation with at least one crosslinking monomer having at least two reactive ethylene functions under ionizing radiation, said crosslinked polyvinyl alcohol hydrogel having 70 to 95% by weight of chains derived from polyvinyl alcohol and 5 to 30% by weight of chains derived from crosslinking monomers and at least part of the $-OH$ groups of the polyvinyl alcohol hydrogel are replaced by $-OSO_3H$ groups comprising the steps of:

(a) crosslinking the polyvinyl alcohol by irradiating by means of ionizing rays a mixture of 70 to 95% by weight polyvinyl alcohol and 5 to 30% by weight of crosslinking monomers, in an oxygen-free atmosphere and (b) subjecting the thus obtained crosslinked polyvinyl alcohol to a chlorosulphonation treatment to replace at least part of the $-OH$ groups of the polyvinyl alcohol by $-OSO_3H$ groups.

10. A process according to claim 9, wherein during stage (a), the polyvinyl alcohol is an aqueous solution.

11. A process according to claim 9, wherein the polyvinyl alcohol concentration of the aqueous solution is 25 to 30% by weight.

12. A process according to claim 9, wherein the starting polyvinyl alcohol in a 4% aqueous solution has a viscosity of 3.5 to 5 mPa.s.

13. A process according to claim 9, wherein irradiation is carried out by means of gamma rays, the total radiations dose being 8 to 16 Mrad.

14. A process according to claim 9, wherein the chlorosulphonation treatment consists of preparing a complex of chlorosulphonic acid and pyridine, then contacting said complex with the crosslinked polyvinyl alcohol.

* * * * *